United States Patent [19]

Krämer et al.

[11] 4,239,766
[45] Dec. 16, 1980

[54] COMBATING FUNGI WITH 1-(4-PHENOXY)-3,3-DIMETHYL-2-(N-HALOGENOALKYLMERCAPTO-CARBAMOYLOXY)-1-(1,2,4-TRIAZOL-1-YL)-BUTANES

[75] Inventors: Wolfgang Krämer; Karl H. Büchel, both of Wuppertal; Engelbert Kühle, Bergisch-Gladbach; Paul-Ernst Frohberger, Leverkusen; Wilhelm Beandes, Leichlingen, all of Fed. Rep. of Germany

[73] Assignee: Bayer Aktiengesellschaft, Leverkusen, Fed. Rep. of Germany

[21] Appl. No.: 46,283

[22] Filed: Jun. 7, 1979

[30] Foreign Application Priority Data

Jun. 26, 1978 [DE]  Fed. Rep. of Germany ....... 2827968

[51] Int. Cl.³ .................... A01N 47/12; C07D 249/08
[52] U.S. Cl. .................................... 424/269; 424/245; 548/101; 548/262
[58] Field of Search ............... 424/269, 245; 548/101, 548/262

[56] References Cited

U.S. PATENT DOCUMENTS

| 2,553,770 | 5/1951 | Kittleson | 424/274 |
|---|---|---|---|
| 2,553,775 | 5/1951 | Hawley et al. | 424/270 |
| 3,285,929 | 11/1966 | Klawke et al. | 548/210 |
| 3,499,030 | 3/1970 | Kuhle et al. | 548/210 |
| 4,145,428 | 3/1979 | Kramer et al. | 548/262 |

OTHER PUBLICATIONS

Horsfall, "Principles of Fungicidal Action", (1956, Waltham, Mass.), pp. 61, 67, 73.

*Primary Examiner*—Alton D. Rollins
*Attorney, Agent, or Firm*—Sprung, Felfe, Horn, Lynch & Kramer

[57] ABSTRACT

A 1-(4-phenoxy)-3,3-dimethyl-2-(N-halogenoalkylmercapto-carbamoyloxy)-1-(1,2,4-triazol-1-yl)-butane of the formula

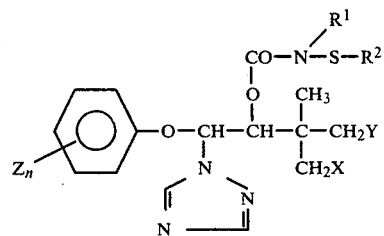

in which
R$^1$ is alkyl or optionally substituted phenyl,
R$^2$ is halogenoalkyl,
X is hydrogen or halogen,
Y is hydrogen or halogen,
Z each independently is alkyl, cycloalkyl, alkoxy, alkylthio, halogenoalkyl, alkoxycarbonyl, optionally substituted phenyl, phenoxy or phenylalkyl, cyano or nitro, and
n is 0, 1, 2, 3, 4 or 5, and physiologically acceptable acid addition salts and metal salt complexes thereof which possess fungicidal properties.

12 Claims, No Drawings

COMBATING FUNGI WITH 1-(4-PHENOXY)-3,3-DIMETHYL-2-(N-HALOGENOALKYLMERCAPTO-CARBAMOYLOXY)-1-(1,2,4-TRIAZOL-1-YL)-BUTANES

The present invention relates to and has for its objects the provision of particular new 1-(4-phenoxy)-3,3-dimethyl-2-(N-halogenoalkylmercapto-carbamoyloxy)-1-(1,2,4-triazol-1-yl)-butanes which possess fungicidal properties, active compositions in the form of mixtures of such compounds with solid and liquid dispersible carrier vehicles, and methods for producing such compounds and for using such compounds in a new way especially for combating pests, e.g. fungi, with other and further objects becoming apparent from a study of the within specification and accompanying examples.

It has already been disclosed that trityl-triazoles, such as triphenyl-(1,2,4-triazol-1-yl)-methane, have a good fungicidal activity (see DE-OS (German Published Specification) No. 1,795,249). It has also already been disclosed that acylated triazolyl-O,N-acetals, such as, in particular, 2-acyloxy-3,3-dimethyl-1-phenoxy-1-(1,2,4-triazol-1-yl)-butanes which are substituted in the phenyl part, display good fungicidal properties (see U.S. Pat. No. 4,195,428). However, the action of these compounds is not always completely satisfactory, especially when low amounts and concentratitons are used.

The present invention now provides, as new compounds, the sulphenylated carbamoyl-triazolyl-O,N-acetals of the general formula

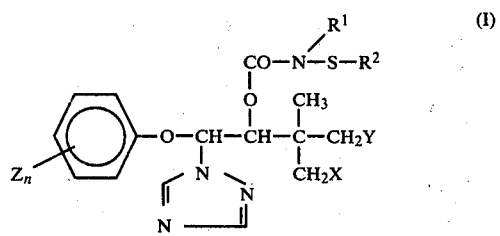

in which
R$^1$ represents alkyl or optionally substituted phenyl,
R$^2$ represents halogenoalkyl,
X represents hydrogen or halogen,
Y represents hydrogen or halogen,
Z represents halogen, alkyl, cycloalkyl, alkoxy, alkylthio, halogenoalkyl, alkoxycarbonyl, optionally substituted phenyl, phenoxy or phenylalkyl, cyano or nitro and
n represents 0, 1, 2, 3, 4 or 5, the substituents Z being selected independently of one another when n is 2-5, and physiologically acceptable acid addition salts and metal salt complexes thereof.

Surprisingly, the sulphenylated carbamoyl-triazolyl-O,N-acetals according to the invention exhibit a considerably higher fungicidal activity, in particular against varieties of rust and powdery mildew, than the acylated triazolyl-O,N-acetals known from the state of the art, which are closely related compounds chemically and from the point of view of their action, and than triphenyl-(1,2,4-triazol-1-yl)-methane, which is a compound of the same type of action. The substances according to the invention thus represent an enrichment of the art.

Preferably, R$^1$ represents straight-chain or branched alkyl with 1 to 4 carbon atoms or optionally substituted phenyl, the substituents being selected from halogen, alkyl with 1 or 2 carbon atoms, cyano and nitro;

R$^2$ represents halogenoalkyl with 1 or 2 carbon atoms and up to 5 halogen atoms (especially fluorine and chlorine atoms);

X and Y, which may be identical or different, each represent hydrogen or halogen;

Z represents halogen, cyano, nitro, straight-chain or branched alkyl with up to 4 carbon atoms, cycloalkyl with 5 to 7 carbon atoms, halogenoalkyl with up to 2 carbon atoms and up to 5 halogen atoms (especially fluorine and chlorine atoms), alkoxycarbonyl with a total of up to 5 carbon atoms, alkoxy with up to 2 carbon atoms, alkylthio with up to 2 carbon atoms, optionally substituted phenyl, optionally substituted phenoxy or optionally substituted phenylalkyl with 1 or 2 carbon atoms in the alkyl part, the substituents on the phenyl nucleus of the three last-mentioned radicals Z being selected from halogen, amino, cyano, nitro and alkyl with 1 or 2 carbon atoms, the alkyl part of the phenylalkyl radical Z being optionally substituted by alkylcarbonyloxy with a total of up to 3 carbon atoms; and n represents 0, 1, 2 or 3.

The compounds of the formula (I) have two asymmetric carbon atoms; they can therefore exist in the erythro form and in the threo form. In both cases, they are present predominantly in the form of racemates.

Particularly preferred compounds of the formula (I) are those in which R$^1$ represents methyl, or phenyl which is optionally substituted by chlorine or methyl; R$^2$ represents trifluoromethyl, chlorodifluoromethyl, dichlorofluoromethyl or trichloromethyl; X and Y, which may be identical or different, each represent hydrogen, fluorine chlorine or bromine; Z represents fluorine, chlorine, bromine, methyl, ethyl, cyclohexyl, methoxy, methylthio, trifluoromethyl, methoxycarbonyl, cyano, nitro or a phenyl, phenoxy or benzyl radical which is optionally substituted by chlorine or methyl; and n represents 0, 1 or 2.

In addition to the compounds listed in the preparative examples, the following compounds of the general formula

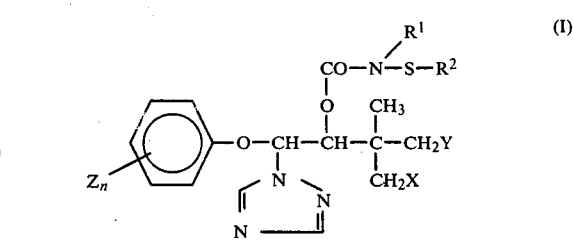

with the following substituent meanings may also be mentioned specifically:

TABLE 1

| R$^1$ | R$^2$ | X | Y | Z$_n$ |
|---|---|---|---|---|
| CH$_3$ | CCl$_3$ | H | H | — |
| CH$_3$ | CCl$_3$ | H | H | 4-Br |
| CH$_3$ | CCl$_3$ | H | H | 4-F |
| CH$_3$ | CCl$_3$ | H | H | 2,4-Cl$_2$ |
| CH$_3$ | CCl$_3$ | H | H | 2-CH$_3$, 4-Cl |
| CH$_3$ | CCl$_3$ | H | H | 2-C$_6$H$_5$ |
| C$_6$H$_5$ | CCl$_3$ | H | H | — |

TABLE 1-continued

| R¹ | R² | X | Y | $Z_n$ |
|---|---|---|---|---|
| Ph | CCl₃ | H | H | 4-Cl |
| Ph | CCl₃ | H | H | 4-Ph |
| Ph | CCl₃ | H | H | 2-Ph |
| Ph | CCl₃ | H | H | 4-Br |
| Ph | CCl₃ | H | H | 4-F |
| Ph | CCl₃ | H | H | 2,4-Cl₂ |
| Ph | CCl₃ | H | H | 2-CH₃, 4-Cl |
| CH₃ | CCl₂F | H | H | — |
| CH₃ | CCl₂F | H | H | 4-Br |
| CH₃ | CCl₂F | H | H | 4-F |
| CH₃ | CCl₂F | H | H | 2,4-Cl₂ |
| CH₃ | CCl₂F | H | H | 2-CH₃, 4-Cl |
| CH₃ | CCl₂F | H | H | 2-Ph |
| Ph | CCl₂F | H | H | — |
| Ph | CCl₂F | H | H | 4-Cl |
| Ph | CCl₂F | H | H | 4-Ph |
| Ph | CCl₂F | H | H | 2-Ph |
| Ph | CCl₂F | H | H | 4-Br |
| Ph | CCl₂F | H | H | 4-F |
| Ph | CCl₂F | H | H | 2,4-Cl₂ |
| Ph | CCl₂F | H | H | 2-CH₃, 4-Cl |
| CH₃ | CCl₃ | Cl | H | — |
| CH₃ | CCl₃ | Cl | H | 4-Cl |
| CH₃ | CCl₃ | Cl | H | 4-Ph |
| CH₃ | CCl₃ | Cl | H | 2-Ph |
| CH₃ | CCl₃ | Cl | H | 4-Br |
| CH₃ | CCl₃ | Cl | H | 4-F |
| CH₃ | CCl₃ | Cl | H | 2,4-Cl₂ |
| CH₃ | CCl₃ | Cl | H | 2-CH₃, 4-Cl |
| Ph | CCl₃ | Cl | H | — |
| Ph | CCl₃ | Cl | H | 4-Cl |
| Ph | CCl₃ | Cl | H | 4-Ph |
| Ph | CCl₃ | Cl | H | 2-Ph |
| Ph | CCl₃ | Cl | H | 4-Br |
| Ph | CCl₃ | Cl | H | 4-F |
| Ph | CCl₃ | Cl | H | 2,4-Cl₂ |
| Ph | CCl₃ | Cl | H | 2-CH₃, 4-Cl |
| CH₃ | CCl₂F | Cl | H | — |
| CH₃ | CCl₂F | Cl | H | 4-Cl |
| CH₃ | CCl₂F | Cl | H | 4-Ph |
| CH₃ | CCl₂F | Cl | H | 2-Ph |
| CH₃ | CCl₂F | Cl | H | 4-Br |
| CH₃ | CCl₂F | Cl | H | 4-F |
| CH₃ | CCl₂F | Cl | H | 2,4-Cl₂ |
| CH₃ | CCl₂F | Cl | H | 2-CH₃, 4-Cl |
| Ph | CCl₂F | Cl | H | — |
| Ph | CCl₂F | Cl | H | 4-Cl |
| Ph | CCl₂F | Cl | H | 2-Ph |
| Ph | CCl₂F | Cl | H | 4-Br |
| Ph | CCl₂F | Cl | H | 4-F |
| Ph | CCl₂F | Cl | H | 2,4-Cl₂ |
| Ph | CCl₂F | Cl | H | 2-CH₃, 4-Cl |
| Ph | CCl₂F | Cl | H | 4-Ph |
| CH₃ | CCl₃ | Cl | Cl | 4-Cl |
| CH₃ | CCl₃ | Cl | Cl | 4-Ph |
| CH₃ | CCl₂ | Cl | Cl | 2-Ph |
| CH₃ | CCl₃ | Cl | Cl | — |
| CH₃ | CCl₃ | Cl | Cl | 4-Br |
| CH₃ | CCl₃ | Cl | Cl | 4-F |
| CH₃ | CCl₃ | Cl | Cl | 2,4-Cl₂ |
| CH₃ | CCl₃ | Cl | Cl | 2-CH₃, 4-Cl |
| CH₃ | CCl₂F | Cl | Cl | — |
| CH₃ | CCl₂F | Cl | Cl | 4-Ph |
| CH₃ | CCl₂F | Cl | Cl | 2-Ph |
| CH₃ | CCl₂F | Cl | Cl | 4-Br |
| CH₃ | CCl₂F | Cl | Cl | 4-F |
| CH₃ | CCl₂F | Cl | Cl | 2,4-Cl₂ |
| CH₃ | CCl₂F | Cl | Cl | 2-CH₃, 4-Cl |
| CH₃ | CCl₃ | Br | H | — |
| CH₃ | CCl₃ | Br | H | 4-Cl |
| CH₃ | CCl₃ | Br | H | 4-Ph |
| CH₃ | CCl₃ | Br | H | 2-Ph |
| CH₃ | CCl₃ | Br | H | 4-Br |
| CH₃ | CCl₃ | Br | H | 4-F |
| CH₃ | CCl₃ | Br | H | 2,4-Cl₂ |

TABLE 1-continued

| R¹ | R² | X | Y | $Z_n$ |
|---|---|---|---|---|
| CH₃ | CCl₃ | Br | H | 2-CH₃, 4-Cl |

The invention also provides a process for the preparation of a sulphenylated carbamoyl-triazolyl-O,N-acetal of the formula (I) in which an alcoholate of a 2-hydroxy-1-phenoxy-1-triazolyl-butane, of the general formula

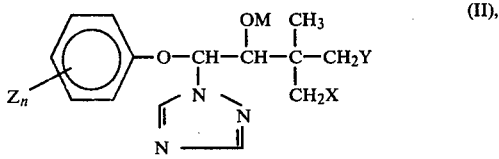

in which
X, Y, Z and n have the meanings stated above and
M represents an alkali metal or a quaternary ammonium or phosphonium group,
is reacted with a sulphenylated carbamoyl fluoride of the general formula

in which
R¹ and R² have the meanings stated above, in the presence of a diluent.

Furthermore, the sulphenylated carbamoyl-triazolyl-O,N-acetals of the formula (I) obtainable according to the invention can be converted into the salts, by reaction with acids, and the corresponding metal salt complexes can be obtained by reaction with metal salts.

If, for example, the sodium alkanolate of 1-(4-chlorophenoxy)-3,3-dimethyl-1-(1,2,4-triazol-1-yl)-butan-2-ol and N-methyl-N-trichloromethylmercaptocarbamoyl fluoride are used as starting substances, the course of the reaction can be represented by the equation which follows:

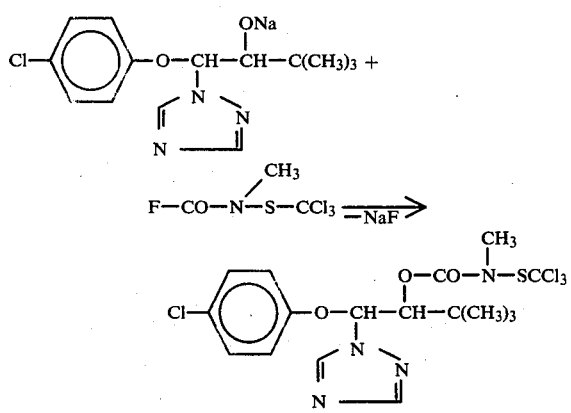

The formula (II) provides a general definition of the alcoholates, to be used as starting substances, of 2-hydroxy-1-phenoxy-1-triazolyl-butanes. In this formula, M preferably represents lithium, sodium, potassium, tetrabutylammonium, N-benzyl-N,N,N-trimethylammonium, hexadecyltrimethylammonium, 2-hydroxyethyl-trimethyl-ammonium, tetraethylammonium, tetramethylammonium, tetra-n-propylammonium, (cyclopropylmethyl)-trimethyl-ammonium, methyltrioctylammonium, N-phenyl-N,N,N-trimethyl-ammonium, N-(4-methylbenzyl)-N,N,N-trimethyl-ammonium, N-benzyl-N,N-dimethyl-N-dodecyl-ammonium, N,N-dibenzyl-N,N-dimethylammonium, benzyl-dimethyl-n-hexadecyl-ammonium, benzyl-dimethyl-tetradecyl-ammonium, benzyl-tributyl-ammonium, benzyl-triethyl-ammonium, butyl-tripropyl-ammonium, octadecyl-trimethyl-ammonium, tetrahexyl-ammonium, tetra-octyl-ammonium, tetra-pentyl-ammonium, tricaprylmethylammonium, hexadecylpyridinium, tetraphenylphosphonium, hexadecyltributyl-phosphonium, ethyl-triphenyl-phosphonium or methyl-triphenyl-phosphonium.

The alcoholates of the formula (II) have not yet been described in the literature. They are obtained by reacting the corresponding 2-hydroxy-1-phenoxy-1-triazolyl-butanes with suitable strong bases, such as alkali metal amides or hydrides or quaternary ammonium hydroxides or phosphonium hydroxides, in an inert solvent. The 2-hydroxy-1-phenoxy-1-triazolyl-butanes mentioned are known (see U.S. Pat. No. 3,952,002, issued Apr. 20, 1976 and U.S. application Ser. No. 964,215, now pending).

Examples which may be mentioned of the 2-hydroxy-1-phenoxy-1-triazolyl-butanes from which the alcoholates of the formula (II) are derived are: 2-hydroxy-3,3-dimethyl-1-phenoxy-1-(1,2,4-triazol-1-yl)-butane, 2-hydroxy-3,3-dimethyl-1-(4-chlorophenoxy)-1-(1,2,4-triazol-1-yl)-butane, 2-hydroxy-3,3-dimethyl-1-(2,4-dichlorophenoxy)-1-(1,2,4-triazol-1-yl)-butane, 2-hydroxy-3,3-dimethyl-1-(4-bromophenoxy)-1-(1,2,4-triazol-1-yl)-butane, 2-hydroxy-3,3-dimethyl-1-(4-biphenylyloxy)-1-(1,2,4-triazol-1-yl)-butane, 2-hydroxy-3,3-dimethyl-1-(2-biphenylyloxy)-1-(1,2,4-triazol-1-yl)-butane, 2-hydroxy-3,3-dimethyl-1-(4'-chloro-4-biphenylyloxy)-1-(1,2,4-triazol-1-yl)-butane, 2-hydroxy-3,3-dimethyl-1-(4-phenoxyphenoxy)-1-(1,2,4-triazol-1-yl)-butane, 2-hydroxy-3,3-dimethyl-1-(4'-chloro-4-phenoxyphenoxy)-1-(1,2,4-triazol-1-yl)-butane, 2-hydroxy-3,3-dimethyl-1-(4-bromophenoxy)-1-(1,2,4-triazol-1-yl)-butane, 2-hydroxy-3,3-dimethyl-1-(4-fluorophenoxy)-1-(1,2,4-triazol-1-yl)-butane, 2-hydroxy-3,3-dimethyl-(4-chloro-2-methylphenoxy)-1-(1,2,4-triazol-1-yl)-butane, 4-chloro-2-hydroxy-3,3-dimethyl-1-phenoxy-1-(1,2,4-triazol-1-yl)-butane, 4-chloro-2-hydroxy-3,3-dimethyl-1-(4-chlorophenoxy)-1-(1,2,4-triazol-1-yl)-butane, 4-chloro-2-hydroxy-3,3-dimethyl-1-(2,4-dichlorophenoxy)-1-(1,2,4-triazol-1-yl)-butane, 4-chloro-2-hydroxy-3,3-dimethyl-1-(4-bromophenoxy)-1-(1,2,4-triazol-1-yl)-butane, 4-chloro-2-hydroxy-3,3-dimethyl-1-(4-biphenylyloxy)-1-(1,2,4-triazol-1-yl)-butane, 4-chloro-2-hydroxy-3,3-dimethyl-1-(2-biphenylyloxy)-1-(1,2,4-triazol-1-yl)-butane, 4-chloro-2-hydroxy-3,3-dimethyl-1-(4'-chloro-4-biphenylyloxy)-1-(1,2,4-triazol-1-yl)-butane, 4-chloro-2-hydroxy-3,3-dimethyl-1-(4-phenoxyphenoxy)-1-(1,2,4-triazol-1-yl)-butane, 4-chloro-2-hydroxy-3,3-dimethyl-1-(4'-chloro-4-phenoxyphenoxy)-1-(1,2,4-triazol-1-yl)-butane, 4-chloro-2-hydroxy-3,3-dimethyl-1-(4-fluorophenoxy)-1-(1,2,4-triazol-1-yl)-butane, 4-chloro-2-hydroxy-3,3-dimethyl-1-(4-chloro-2-methylphenoxy)-1-(1,2,4-triazol-1-yl)-butane, 4-bromo-2-hydroxy-3,3-dimethyl-1-phenoxy-1-(1,2,4-triazol-1-yl)-butane, 4-bromo-2-hydroxy-3,3-dimethyl-1-(4-chlorophenoxy)-1-(1,2,4-triazol-1-yl)-butane, 4-bromo-2-hydroxy-3,3- dimethyl-1-(2,4-dichlorophenoxy)-1-(1,2,4-triazol-1-yl)-butane, 4-bromo-2-hydroxy-3,3-dimethyl-1-(4-bromophenoxy)-1-(1,2,4-triazol-1-yl)-butane, 4-bromo-2-hydroxy-3,3-dimethyl-1-(4-biphenylyloxy)-1-(1,2,4-triazol-1-yl)-butane, 4-bromo-2-hydroxy-3,3-dimethyl-1-(2-biphenylyloxy)-1-(1,2,4-triazol-1-yl)-butane, 4-bromo-2-hydroxy-3,3-dimethyl-1-(4'-chloro-4-biphenylyloxy)-1-(1,2,4-triazol-1-yl)-butane, 4-bromo-2-hydroxy-3,3-dimethyl-1-(4-phenoxyphenoxy)-1-(1,2,4-triazol-1-yl)-butane, 4-bromo-2-hydroxy-3,3-dimethyl-1-(4'-chloro-4-phenoxyphenoxy)-1-(1,2,4-triazol-1-yl)-butane, 4-bromo-2-hydroxy-3,3-dimethyl-1-(4-fluorophenoxy)-1-(1,2,4-triazol-1-yl)-butane, 4-bromo-2-hydroxy-3,3-dimethyl-1-(4-chloro-2-methylphenoxy)-1-(1,2,4-triazol-1-yl)-butane, 4-chloro-3-chloromethyl-2-hydroxy-3-methyl-1-phenoxy-1-(1,2,4-triazol-1-yl)-butane, 4-chloro-3-chloromethyl-2-hydroxy-3-methyl-1-(4-chlorophenoxy)-1-(1,2,4-triazol-1-yl)-butane, 4-chloro-3-chloromethyl-2-hydroxy-3-methyl-1-(2,4-dichlorophenoxy)-1-(1,2,4-triazol-1-yl)-butane, 4-chloro-3-chloromethyl-2-hydroxy-3-methyl-1-(4-bromophenoxy)-1-(1,2,4-triazol-1-yl)-butane, 4-chloro-3-chloromethyl-2-hydroxy-3-methyl-1-(4-biphenylyloxy)-1-(1,2,4-triazol-1-yl)-butane, 4-chloro-3-chloromethyl-2-hydroxy-3-methyl-1-(2-biphenylyloxy)-1-(1,2,4-triazol-1-yl)-butane, 4-chloro-3-chloromethyl-2-hydroxy-3-methyl-1-(4'-chloro-4-biphenylyloxy)-1-(1,2,4-triazol-1-yl)-butane, 4-chloro-3-chloromethyl-2-hydroxy-3-methyl-1-(4-phenoxyphenoxy)-1-(1,2,4-triazol-1-yl)-butane, 4-chloro-3-chloromethyl-2-hydroxy-3-methyl-1-(4'-chloro-4-phenoxyphenoxy)-1-(1,2,4-triazol-1-yl)-butane, 4-chloro-3-chloromethyl-2-hydroxy-3-methyl-1-(4-fluorophenoxy)-1-(1,2,4-triazol-1-yl)-butane and 4-chloro-3-chloromethyl-2-hydroxy-3-methyl-1-(4-chloro-2-methylphenoxy)-1-(1,2,4-triazol-1-yl)-butane.

Sulphenylated carbamoyl fluorides of the formula (III) are known (see German Pat. No. 1,297,095 and U.S. Pat. No. 3,639,471), and they can be prepared by processes which are generally customary and known. They are obtained, for example, by reacting the corresponding carbamic acid fluorides with the corresponding sulphenyl chlorides.

Examples which may be mentioned of starting substances of the formula (III) are: N-methyl-N-trichloromethylmercapto-carbamoyl fluoride, N-methyl-N-dichloro-fluoromethylmercapto-carbamoyl fluoride, N-methyl-N-chlorodifluoromethylmercapto-carbamoyl fluoride, N-methyl-N-trifluoromethylmercapto-carbamoyl fluoride, N-phenyl-N-trifluoromethylmercapto-carbamoyl fluoride, N-phenyl-N-chlorodifluoromethylmercapto-carbamoyl fluoride, N-phenyl-N-dichlorofluoromethylmercapto-carbamoyl fluoride and N-phenyl-N-trichloromethylmercapto-carbamoyl fluoride.

Possible diluents for the reaction according to the invention are inert organic solvents, especially ethers, such as tetrahydrofuran and dioxane; benzene; and, in some cases, chlorinated hydrocarbons, such as chloroform, methylene chloride or carbon tetrachloride.

The reaction temperatures can be varied within a substantial range. In general, the reaction is carried out between 20° and 150° C., preferably at the boiling point of the solvent, for example between 60° and 100° C.

Equimolar amounts of the reactants are preferably used in carrying out the process according to the invention. In order to isolate the end products, the reaction mixture is freed from the solvent, and water and an organic solvent are added to the residue. The organic phase is separated off and worked up and purified in the customary manner, and a salt or a metal salt complex is optionally prepared.

In a preferred embodiment, the appropriate procedure is to use a 2-hydroxy-3,3-dimethyl-1-phenoxy-1-(1,2,4-triazol-1-yl)-butane derivative as the starting material, to convert this into an alkali metal alcoholate of the formula (II) in a suitable inert organic solvent by means of an alkali metal hydride or alkali metal amide, and to react the alcoholate immediately with a carbamoyl fluoride of the formula (III) without isolation, the compounds of the formula (I) according to the invention being obtained in one operation, alkali metal fluorides being eliminated.

According to a further preferred embodiment, the reaction of the 2-hydroxy-3,3-dimethyl-1-phenoxy-1-(1,2,4-triazol-1-yl)-butane derivative with the carbamoyl fluoride of the formula (III) is carried out directly in the presence of potassium fluoride or 4-dimethylaminopyridine as the base, and, when pyridine is used as the base, this is added dropwise to the reaction mixture and not initially introduced from the beginning.

All the physiologically acceptable acids can be used for the preparation of acid addition salts of the compounds of the formula (I). Preferred acids include the hydrogen halide acids (for example hydrobromic acid and especially hydrochloric acid), phosphoric acid, nitric acid, sulphuric acid, monofunctional and bifunctional carboxylic acids and hydroxycarboxylic acids (for example acetic acid, maleic acid, succinic acid, fumaric acid, tartaric acid, citric acid, salicylic acid, sorbic acid and lactic acid) and sulphonic acids (for example p-toluenesulphonic acid and 1,5-naphthalenedisulphonic acid).

The salts of the compounds of the formula (I) can be obtained in a simple manner by customary salt formation methods, for example by dissolving a compound of the formula (I) in a suitable inert solvent and adding the acid, for example hydrochloric acid, and can be isolated in a known manner, for example by filtration, and optionally purified by washing with an inert organic solvent.

Salts of metals of main groups II to IV and of subgroups I and II and IV to VIII can be used for the preparation of metal salt complexes of the compounds of the formula (I), examples of such metals being copper, zinc, manganese, magnesium, tin, iron and nickel. Possible anions of the salts are those which are derived from physiological acids, preferably the hydrogen halide acids (for example hydrochloric acid and hydrobromic acid), phosphoric acid, nitric acid and sulphuric acid.

The metal salt complexes of the compounds of the formula (I) can be obtained in a simple manner by customary processes, thus, for example, by dissolving the metal salt in alcohol, for example ethanol, and adding the solution to the compound of the formula (I). The metal salt complexes can be isolated in a known manner, for example by filtration, and optionally purified by recrystallization.

The active compounds according to the invention display a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating those fungi which cause powdery mildew diseases, especially for combating Podosphaera species, for example against the powdery mildew of apple causative organism (*Podosphaera leucotricha*), and Erysiphe species, for example against the powdery mildew of cucumber causative organism (*Erysiphe cichoracearum*) or the powdery mildew of barley or powdery mildew of cereal causative organism (*Erysiphe graminis*); and for combating other cereal diseases, such as cereal rust. It should be particularly emphasised that the active compounds according to the invention not only develop a protective action, but in some cases also have a systemic action. Thus, it is possible to protect plants against fungal attack when the active compound is fed to the above-ground parts of the plant via the soil and the root or via the seed.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations or in the various use forms as a mixture with other active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, slurrying, brushing on, dusting, scattering, dry dressing, moist dressing, wet dressing, slurry dressing or encrusting.

For the treatment of parts of plants, the active compound concentrations in the use forms can be varied within a substantial range. They are, in general, from 1 to 0.0001% by weight, preferably from 0.5 to 0.001%.

In the treatment of seed, amounts of active compound of 0.001 to 50 g, preferably 0.01 to 10 g, are generally employed per kilogram of seed.

For the treatment of soil, active compound concentrations of 0.00001 to 0.1% by weight, preferably 0.0001 to 0.02%, are generally required at the place of action.

The present invention also provides a fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

The preparation of the novel compounds is shown in the following illustrative example:

EXAMPLE 1

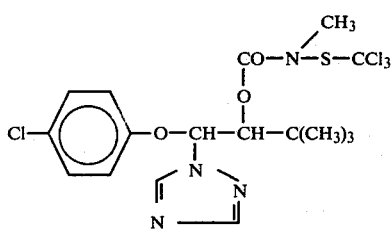

22.3 g (0.075 mol) of 1-(4-chlorophenoxy)-3,3-dimethyl-1-(1,2,4-triazol-1-yl)-butan-2-ol, in the form of the pure diastereomer, were dissolved in 200 ml of tetrahydrofuran and the solution was added dropwise to 2.3 g of 80% pure sodium hydride in 150 ml of tetrahydrofuran at room temperature, while stirring. Thereafter, the mixture was stirred at 50° C. for 12 hours. After cooling, 17 g (0.075 mol) of N-methyl-N-trichloromethylmercaptocarbamoyl fluoride were added dropwise, at room temperature, to the sodium salt thus obtained, whereupon the temperature rose to about 35° C. The mixture was then heated under reflux for 16 hours, left to cool and concentrated by distilling off the solvent. The oily residue was taken up in 500 ml of methylene chloride, washed twice with 1,000 ml of water each time, dried over sodium sulphate and concentrated. The oil which remained was taken up in 300 ml of isopropyl ether, whereupon it crystallized out. 14.5 g (37% of theory) of 1-(4-chlorophenoxy)-3,3-dimethyl-2-(N-methyl-N-trichloromethylmercapto-carbamoyloxy)-1-(1,2,4-triazol-1-yl)-butane were obtained in the form of the pure diastereomer of melting point 110°–112° C.

The following compounds of the general formula

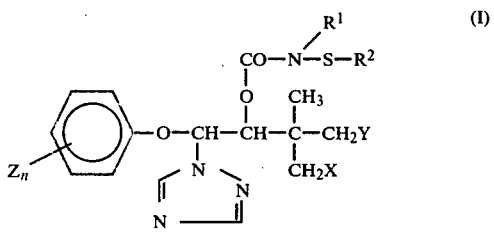

were obtained analogously:

TABLE

| Compound No. | $R^1$ | $R^2$ | X | Y | $Z_n$ | Melting point (°C.) |
|---|---|---|---|---|---|---|
| 2 | $CH_3$ | $-CCl_3$ | H | H | 4-⟨O⟩ | 127-29 (A-Form) |
| 3 | $CH_3$ | $-CCl_2F$ | H | H | 4-⟨O⟩ | 99-101 (A-Form) |
| 4 | $CH_3$ | $-CCl_2F$ | H | H | 4-Cl | 84-89 (A-Form) |
| 5 | $CH_3$ | $-CCl_3$ | H | H | 4-Br | 112 |
| 6 | ⟨O⟩ | $-CCl_2F$ | H | H | 4-Br | 211 (× ½ NDS) (A-Form) |
| 7 | ⟨O⟩ | $-CCl_2F$ | H | H | 2,4-$Cl_2$ | 250 (× ½ NDS) (A-Form) |

NDS = 1,5-naphthalenedisulfonic acid
A-Form and B-Form = in each case one of the two possible geometric isomers The fungicidal activity of the compounds of this invention is illustrated by the following examples wherein the compounds according to the present invention are each identified by the number (given in brackets) from Example 1.

EXAMPLE 2

Shoot treatment test/powdery mildew of cereals (leaf-destructive mycosis)/protective To produce a suitable preparation of active compound, 0.25 part by weight of active compound was taken up in 25 parts by weight of dimethylformamide and 0.06 part by weight of alkylaryl polyglycol ether; 975 parts by weight of water were then added. The concentrate was diluted with water to the desired final concentration of the spray liquor.

To test for protective activity, single-leaved young barley plants of the Amsel variety were sprayed with the preparation of active compound until dew-moist. After drying, the barley plants were dusted with spores of Erysiphe graminis var. hordei.

After 6 days' dwell time of the plants at a temperature of 21–22 deg. C. and 80–90% atmospheric humidity the occurrence of mildew pustules on the plants was evaluated. The degree of infection was expressed as a percentage of the infection of the untreated control plants. The more active the compound, the lower is the degree of mildew infection.

In this test, for example, the following compounds exhibited a very good action which was superior to that of the compounds known from the prior art: (2), (3), (4) and (1).

EXAMPLE 3

Powdery mildew of barley (Erysiphe graminis var. hordei) (fungal disease of cereal shoots)/systemic The active compound was used as a pulverulent seed treatment agent. This was prepared by extending the particular active compound with a mixture of equal parts by weight of talc and kieselguhr to give a finely pulverulent mixture of the desired concentration of active compound.

For the treatment of seed, barley seed was shaken with the extended active compound in a closed glass bottle. The seed was sown at the rate of 3×12 grains in flowerpots, 2 cm deep in a mixture of one part by volume of Fruhstorfer standard soil and one part by volume of quartz sand. The germination and emergence took place under favorable conditions in a greenhouse. 7 days after sowing, when the barley plants had developed their first leaf, they were dusted with fresh spores of Erysiphe graminis var. hordei and grown on at 21–22 deg. C. and 80–90% relative atomspheric humidity and 16 hours' exposure to light. The typical mildew pustules formed on the leaves over the course of 6 days.

The degree of infection was expressed as a percentage of the infection of the untreated control plants. The more active the compound, the lower is the degree of mildew infection.

In this test, for example, the following compounds exhibited a very good action which was superior to that of the compounds known from the prior art: (2), (4) and (1).

EXAMPLE 4

Shoot treatment test/cereal rust (leaf-destructive mycosis)/protective

To produce a suitable preparation of active compound, 0.25 part by weight of active compound was taken up in 25 parts by weight of dimethylformamide and 0.06 part by weight of alkylaryl polyglycol ether and then 975 parts by weight of water were added. The concentrate was diluted with water to the desired final concentration of the spray liquor.

To test the protective activity, one-leaved young wheat plants of the Michigan Amber variety were inoculated with a uredospore suspension of Puccinia recondita in 0.1% strength aqueous agar. After the spore suspension had dried on, the wheat plants were sprayed with the preparation of active compound until dew-moist and were placed, for incubation, in a greenhouse for 24 hours at about 20 deg. C. and 100% relative atmospheric humidity.

After 10 days' dwell time of the plants at a temperature of 20 deg. C. and 80–90% atmospheric humidity, the occurrence of rust pustules on the plant was evaluated. The degree of infection was expressed as a percentage of the infection of the untreated control plants.

The more active the compound, the lower is the degree of rust infection.

In this test, for example, the following compounds exhibited a very good action which was superior to that of the compounds known from the prior art: (2), (3), (4) and (1).

EXAMPLE 5

Erysiphe test (cucumber)/protective

Solvent: 4.7 parts by weight of acetone
Emulsifier: 0.3 part by weight of alkylaryl polyglycol ether
Water: 95 parts by weight The amount of the active compound required for the desired concentration of active compound in the spray liquid was mixed with the stated amount of solvent and the concentrate was diluted with the stated amount of water containing the stated amount of emulsifier.

Young cucumber plants with about three foliage leaves were sprayed with the spray liquid until dripping wet. The cucumber plants remained in a greenhouse for 24 hours to dry. They were then, for the purpose of inoculation, dusted with conidia of the fungus Erysiphe cichoracearum. The plants were subsequently placed in a greenhouse at 23-24 degrees C. and at a relative atmospheric humidity of about 75%.

After 12 days, the infection of the cucumber plants was determined. The assessment data were converted to percent infection.

In this test, for example, the following compounds exhibited a very good action which was superior to that of the compounds known from the prior art: (2) and (3).

EXAMPLE 6

Podosphaera test (apple)/protective

Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the stated amount of emulsifier.

Young apple seedlings in the 4–6 leaf stage were sprayed with the spray liquid until dripping wet. The plants remained in a greenhouse for 24 hours at 20 deg. C. and at a relative atmospheric humidity of 70%. They were then inoculated by dusting the conidia of the apple powdery mildew causative organism (Podosphaera leucotricha) and placed in a greenhouse at a temperature of 21-23 deg. C. and at a relative atmospheric humidity of about 70%.

10 days after the inoculation, the infection of the seedlings was determined.

In this test, for example, the following compounds exhibited a very good action which was superior to that of the compounds known from the prior art: (3) and (1).

It will be appreciated that the instant specification and examples are set forth by way of illustration and not limitation, and that various modifications and changes may be made without departing from the spirit and scope of the present invention.

What is claimed is:

1. A 1-(4-phenoxy)-3,3-dimethyl-2-(N-halogenoalkyl-mercapto-carbamoyloxy)-1-(1,2,4-triazol-1-yl)-butane of the formula

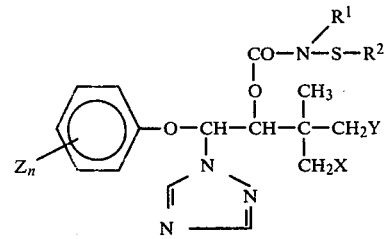

in which
R$^1$ is alkyl with 1 to 4 carbon atoms, phenyl or phenyl substituted with halogen, alkyl with 1 or 2 carbon atoms, cyano or nitro,
R$^2$ is halogenoalkyl with 1 or 2 carbon atoms and up to 5 halogen atoms,
X is hydrogen or halogen,
Y is hydrogen or halogen,
Z each independently is halogen; cyano; nitro; alkyl with up to 4 carbon atoms; cycloalkyl with 5 to 7 carbon atoms; halogenoalkyl with up to 2 carbon atoms and up to 5 halogen atoms; alkoxycarbonyl with a total of up to 5 carbon atoms; alkoxy with up to 2 carbon atoms; alkylthio with up to 2 carbon atoms; or optionally substituted phenyl, optionally substituted phenoxy or optionally substituted phenylalkyl with 1 or 2 carbon atoms in the alkyl part, the optional substituents on the phenyl nuclei being selected from halogen, amino, cyano, nitro and alkyl with 1 or 2 carbon atoms, the alkyl part of the phenylalkyl radical being optionally substituted by alkylcarbonyloxy with a total of up to 3 carbon atoms; and n is 0,1,2,3,4 or 5, and physiologically acceptable acid addition salts and metal salt complexes thereof.

2. A compound according to claim 1, in which n is 0,1,2 or 3.

3. A compound according to claim 1, in the form of an acid-addition salt of a hydrogen halide acid, phosphoric acid, sulphuric acid, nitric acid, sulphonic acid or monofunctional or bifunctional carboxylic or hydroxycarboxylic acids.

4. A compound according to claim 1, in the form of a metal-salt complex, the metal being selected from main groups II to IV and subgroups I, II and IV to VIII of the Periodic Table and the anion of the salt being derived from a halogen halide acid, sulphuric acid, nitric acid or phosphoric acid.

5. A compound according to claim 1, wherein such compound is 1-(4-chlorophenoxy)-3,3-dimethyl-2-(N-methyl-N-trichloromethylmercapto-carbamoyloxy)-1-(1,2,4-triazol-1-yl)-butane of the formula

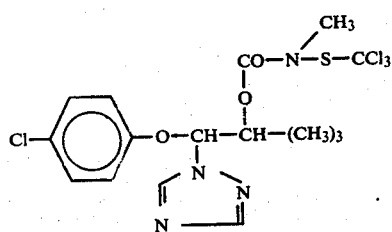

6. A compound according to claim 1, wherein such compound is 1-(4-biphenyloxy)-3,3-dimethyl-2-(N-methyl-N-dichlorofluoromethylmercapto-carbamoyloxy)-1-(1,2,4-triazol-1-yl)-butane of the formula

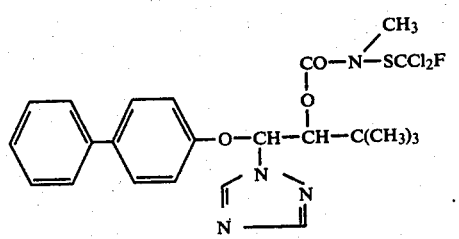

7. A compound according to claim 1, wherein such compound is 1-(4-chlorophenoxy)-3,3-dimethyl-2-(N-methyl-N-dichlorofluoromethylmercapto-carbamoyloxy)-1-(1,2,4-triazol-1-yl)-butane of the formula

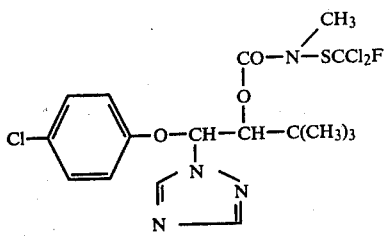

8. A compound according to claim 1, wherein such compound is 1-(4-bromophenoxy)-3,3-dimethyl-2-(N-phenyl-N-dichlorofluoromethylmercapto-carbamoyloxy)-1-(1,2,4-triazol-1-yl)-butane of the formula

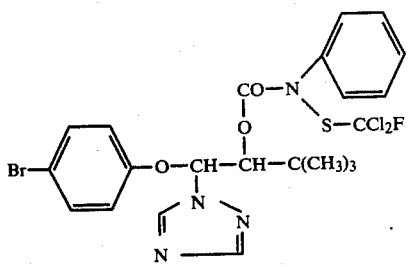

9. A compound according to claim 1, wherein such compound is 1-(2,4-dichlorophenoxy)-3,3-dimethyl-2-(N-phenyl-N-dichlorofluoromethylmercapto-carbamoyloxy)-1-(1,2,4-triazol-1-yl)-butane of the formula

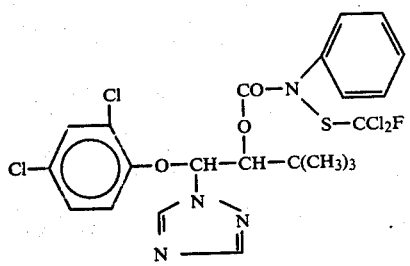

10. A fungicidal composition containing as active ingredient a fungicidally effective amount of a compound according to claim 1 in admixture with a diluent.

11. A method of combating fungi which comprises applying to the fungi, or to a habitat thereof, a fungicidally effective amount of a compound according to claim 1.

12. The method according to claim 11, in which the compound is
1-(4-chlorophenoxy)-3,3-dimethyl-2-(N-methyl-N-trichloromethylmercapto-carbamoyloxy)-1-(1,2,4-triazol-1-yl)-butane,
1-(4-biphenyloxy)-3,3-dimethyl-2-(N-methyl-N-dichlorofluoromethylmercapto-carbamoyloxy-1-(1,2,4-triazol-1-yl)-butane,
1-(4-chlorophenoxy)-3,3-dimethyl-2-(N-methyl-N-dichlorofluoromethylmercapto-carbamoyloxy)-1-(1,2,4-triazol-1-yl)-butane,
1-(4-bromophenoxy)-3,3-dimethyl-2-(N-phenyl-N-dichlorofluoromethylmercapto-carbamoyloxy-1-(1,2,4-triazol-1-yl)-butane, or
1-(2,4-chlorophenoxy)-3,3-dimethyl-2-(N-phenyl-N-dichlorofluoromethylmercapto-carbamoyloxy-1-(1,2,4-triazol-1-yl)-butane,
and it is applied to plants, seed or soil.

* * * * *